United States Patent
Kaercher et al.

(10) Patent No.: US 8,876,805 B2
(45) Date of Patent: Nov. 4, 2014

(54) MEDICAL INSTRUMENT

(71) Applicants: Daniel Kaercher, Radolfzell (DE); Jochen Stefan, Wald (DE)

(72) Inventors: Daniel Kaercher, Radolfzell (DE); Jochen Stefan, Wald (DE)

(73) Assignee: Karl Storz GmbH & Co. KG (DE)

( * ) Notice: Subject to any disclaimer, the term of this patent is extended or adjusted under 35 U.S.C. 154(b) by 120 days.

(21) Appl. No.: 13/734,740

(22) Filed: Jan. 4, 2013

(65) Prior Publication Data

US 2013/0172859 A1 Jul. 4, 2013

(30) Foreign Application Priority Data

Jan. 4, 2012 (DE) .................... 10 2012 200 073

(51) Int. Cl.
*A61B 17/00* (2006.01)
*A61B 17/29* (2006.01)

(52) U.S. Cl.
CPC . *A61B 17/00234* (2013.01); *A61B 2017/00464* (2013.01); *A61B 2017/292* (2013.01); *A61B 2017/00477* (2013.01); *A61B 17/2909* (2013.01)
USPC .............. 606/1; 606/205; 606/207; 294/106; 294/203

(58) Field of Classification Search
USPC .............. 606/207, 110, 1, 167, 205; 294/106, 294/115, 88
See application file for complete search history.

(56) References Cited

U.S. PATENT DOCUMENTS

| | | | | |
|---|---|---|---|---|
| 4,784,422 | A * | 11/1988 | Jones et al. | 294/106 |
| 5,571,137 | A * | 11/1996 | Marlow et al. | 606/207 |
| 5,618,308 | A * | 4/1997 | Holmes et al. | 606/205 |
| 6,358,267 | B1 * | 3/2002 | Murakami et al. | 606/205 |
| 8,016,856 | B2 * | 9/2011 | Lavelle et al. | 606/205 |
| 8,297,673 | B2 * | 10/2012 | Waldorf et al. | 294/203 |
| 2008/0294192 | A1 * | 11/2008 | Stefan et al. | 606/205 |
| 2011/0295242 | A1 * | 12/2011 | Spivey et al. | 606/1 |

FOREIGN PATENT DOCUMENTS

| | | |
|---|---|---|
| DE | 102004025041 A1 | 12/2005 |
| DE | 102006038515 A1 | 2/2008 |
| DE | 102007021658 A1 | 11/2008 |
| WO | 2008005433 A1 | 1/2008 |
| WO | 2009046490 A1 | 4/2009 |

* cited by examiner

*Primary Examiner* — William Thomson
*Assistant Examiner* — Victor Shapiro
(74) *Attorney, Agent, or Firm* — St. Onge Steward Johnston & Reens LLC

(57) ABSTRACT

A transmission adapter for a medical instrument having a shaft, a transmission element that can move within the shaft and an operating device with a first part, which can be mechanically rigidly coupled with a proximal end of the shaft, and a second part, which can move with respect to the first part, includes a first coupling for releasable mechanical coupling with the second part of the operating device and a second coupling for releasable mechanical coupling with a proximal end of the transmission element.

15 Claims, 5 Drawing Sheets

MEDICAL INSTRUMENT

FIELD OF THE INVENTION

The present invention relates to a medical instrument having a shaft, an operating device on the proximal end of the shaft, and a transmission element that can move within the shaft. In particular, the present invention relates to the capacity of an operating device to be combined with transmission elements of different configurations.

BACKGROUND OF THE INVENTION

Directives for the cleaning and sterilization of reusable medical instruments, and in particular surgical instruments, pose high requirements, which require the surgical instruments to be capable of being dismantled. In particular, the shaft and the operating device, as a rule, can be separated from one another. The operating device comprises as a rule at least two gripping members that can be moved with respect to one another, of which one is coupled with the shaft and the other with a transmission rod that is positioned in the shaft. A movement of the two gripping members in relation to one another results in a movement of the transmission rod within the shaft.

The proximal end of the transmission rod is configured, in particular, as a coupling element for releasable mechanical coupling with a gripping member of the operating device. With different shaft diameters, transmission rods with different cross-sections are used. In particular when the transmission rod is connected with a tool that can be separated from the shaft and therefore can be withdrawn out of the shaft in the distal direction, the size of the coupling element on the proximal end of the transmission rod depends on the cross-section of the shaft.

With medical instruments for micro-invasive procedures, there is a trend toward constantly thinner shafts. This requires constantly smaller coupling elements at the proximal ends of the transmission rods. Therefore, operating devices that conventionally retained the same structure for many different medical instruments cannot continue to be used without modification. Instead, the operating devices must be modified and in the worst case must be constantly adjusted to constantly smaller coupling elements at proximal ends of transmission rods.

SUMMARY OF THE INVENTION

An object of the present invention consists in providing an improved medical instrument and making possible a combination of different shafts and different transmission elements with one and the same operating device, in particular with a conventional operating device.

Embodiments of the present invention are based on the idea of providing a transmission adapter that can be coupled, on the one hand, with the proximal end of a transmission element in a shaft for a medical instrument and, on the other hand, with an operating device for a medical instrument. In particular, one transmission adapter is foreseen in each case for a number of different transmission elements or for a number of transmission elements with differently configured couplings at their proximal ends. In each case, a distal end or a coupling on the distal end of the transmission adapter is adjusted to a particular configuration of the proximal end of a transmission element, and the proximal ends of the transmission adapter are equal and in particular are adjusted to a standard operating device.

A transmission adapter for a medical instrument, having a shaft, a transmission element that is movable in the shaft, and an operating device with a first part that can be mechanically rigidly coupled with a proximal end of the shaft, and a second part that is movable with respect to the first part, includes a first coupling for releasable mechanical coupling with the second part of the operating device and a second coupling for releasable mechanical coupling with a proximal end of the transmission element.

The transmission adapter, in particular, is a component of a medical instrument or is foreseen and configured together with other components to constitute a medical instrument. The shaft is straight or curved, partly or completely rigid or partly or completely reshapeable elastically or sculpturally. The transmission element is movable in the shaft by translational and/or rotational means in order to transmit tractive or pressure force and/or torque between the operating device and a distal end of the shaft, in particular a tool on the distal end of the shaft.

The first and second parts of the operating device, in particular, are configured in similar manner as the gripping members of a scissors and are movable with respect to one another by the fingers of one hand. Alternatively, the first and second parts of the operating device are configured in similar manner as the gripping members of a forceps. Alternatively, the operating device comprises a third member, which is configured and disposed in particular symmetrically to the second part of the operating device, such that the second and third parts of the operating device are configured for releasable and common mechanical coupling with the first coupling of the transmission adapter. This latter configuration of the operating device can resemble the structure that is familiar from needle holders.

The operating device and, in particular, its first part are configured, for example, for a releasable catch-locking connection with the proximal end of a shaft. The second part of the operating device, in particular, is connected by a joint (for example, an axle or solid-state joint) with the first part and can pivot with respect to it about a pivot axis perpendicular to the longitudinal axis of a shaft that is to be connected with the operating device.

The first coupling, in particular, is mounted on the proximal end of the transmission adapter and is configured for a jointed mechanical coupling with the second part of the operating device. The second coupling, in particular, is mounted on the distal end of the transmission adapter. Like the transmission element, the transmission adapter is also configured for transmitting a force and/or torque from the second part of the operating device to the proximal end of the transmission element.

The second coupling of the transmission adapter can be configured for positive-locked coupling with a proximal end of any transmission element. The transmission adapter can be adjusted to any transmission element and to any operating device and thus can make possible a combination of any transmission element with any operating device. In particular, constantly thinner shafts and, accordingly, constantly thinner transmission elements with constantly smaller coupling elements at their proximal ends can be combined, in particular, with a conventional operating device, in particular with a standard operating device. Thus it becomes possible to dispense with development costs and costs for new tools for producing operating devices that are adjusted to various transmission elements. Thanks to a narrow range of types and greater numbers of parts, manufacturing parts costs and the expense for inventory and logistics can be reduced.

In addition, the second coupling of the transmission adapter is configured in particular for releasable but rigid mechanical coupling with the proximal end of a transmission rod. As a result of a rigid, non-jointed coupling, it is possible to avoid abrasion and mechanical play such as arise or exist almost inevitably with a jointed configuration. This can allow or simplify additional capacity for miniaturizing transmission elements and their proximal ends. The first coupling can be configured as markedly larger than the proximal end of a transmission element and thus can be markedly less susceptible to abrasion and allow greater mechanical play.

In a transmission adapter as described here, the second coupling includes, in particular, a movable gripper jaw for holding the proximal end of a transmission element by positive locking or friction locking.

The second coupling can include two or more movable gripper jaws. In particular, the second coupling includes a stationary gripper jaw and a movable gripper jaw or two gripper jaws that can move in opposite directions.

The movable gripper jaw, in particular, can pivot about a pivot axis.

The gripper jaw's pivoting ability is generated, for example, by a corresponding bearing or a solid-state joint.

The movable gripper jaw is movable, in particular, along a predetermined pathway.

In particular, guidance is foreseen by means of a link in the form of a slit, groove or ridge, such that a glide surface defines the pathway. The gripper jaw can be simultaneously pivotable around a pivot axis and movable along a predetermined path. In particular, the gripper jaw can be pivoted about a pivot axis, such that an area of the gripper jaw that is distanced from the pivot axis is controlled by means of the link.

One or more gripper jaws can make possible a releasable mechanical coupling of the transmission adapter with a proximal end of given design of a transmission element, said coupling being simple to produce and simultaneously reliable, robust and precise.

A transmission adapter with a movable gripper jaw as described here also includes, in particular, an elastic element that is foreseen and configured to mechanically pre-tense the movable gripper jaw into a position that grips the proximal end of a transmission element.

The elastic element, in particular, is coupled with the movable gripper jaw in such a way that diverting the movable gripper jaw out of the gripping position causes a reshaping of the elastic element that results in a return force and/or a return torque in order to move the movable gripper jaw back into the gripping position. The elastic element can be configured as a single element with the movable gripper jaw and/or part of the transmission adapter. The elastic element has, in particular, the shape of a flat spring or other spring. Alternatively, the elastic element can be configured in the shape of an O-ring or other body made of an elastomer or other elastic material and, when the movable gripper jaw is diverted out of the gripping position, can be stretched, compressed, sheared, and/or twisted.

The elastic element can be configured in order to allow, without additional measures, a sufficiently strong mechanical coupling between the movable gripper jaw and the proximal end of a transmission element. Alternatively, other measures can be foreseen in order to support or lock a mechanical coupling between the movable gripper jaw and the proximal end of a transmission element.

In a transmission adapter as described here, the second coupling, in particular, comprises a rotatable coupling member, such that said rotatable coupling member can be rotated between a first position, in which a mechanical coupling with the proximal end of the transmission element can be established and dissolved, and a second position, in which a mechanical coupling with the proximal end of the transmission element is locked.

The rotatable coupling member, in particular, can rotate about a rotation axis parallel to a longitudinal axis of the transmission element. Here the rotation axis of the rotatable coupling member is, in particular, distanced from the longitudinal axis of the transmission element. Alternatively, the coupling member can be rotatable about a rotation axis perpendicular to a longitudinal axis of the transmission element. Independently of a disposition of the rotation axis parallel or perpendicular to the longitudinal axis of a transmission element that is to be coupled with the coupling member, or in another orientation of the rotation axis, the rotatable coupling member, in particular, comprises a recess or opening for insertion of the proximal end of the transmission element. The opening on the rotatable coupling member comprises a first and a second end. The first end of the opening is configured in such a way that, with the rotatable coupling member in the first position, the proximal end of the transmission element on the first end of the opening can be inserted into the opening and removed from it. The second end of the opening is configured in such a way that, with the rotatable coupling member in the second position, the proximal end of the transmission element on the second end of the opening is held in the opening. In particular, the opening on the first end has a large width or large cross-section and the opening on the second end has a small width or small cross-section. An example is a keyhole-shaped configuration of the opening.

Alternatively, the second coupling on the transmission adapter can be configured for a releasable mechanical coupling, which can be produced or locked and released or unlocked by a relative rotation of the transmission element and the second coupling about an axis parallel to the longitudinal axis of the transmission element.

Alternatively, the second coupling on the transmission adapter can be configured as a catch-lock connection to the proximal end of a transmission element. In particular, a springed catch is foreseen, which is configured to engage in an opening, recess, or indentation on the proximal end of a transmission element. The catch-lock connection by means of the springed catch can be manually releasable by actuation of a pushbutton or other device.

A transmission adapter as described here is, in particular, integrated into a proximal area of a shaft.

In particular, the transmission adapter is integrated into the portion of a shaft that is foreseen and configured for disposition in a corresponding recess in an operating device. The transmission adapter or its space requirement therefore requires no enlargement of the cross-section of the shaft. In addition, on the proximal end of the shaft, soiling of the transmission adapter during use of the shaft is unlikely. Consequently, the cleaning of the shaft with the transmission adapter is simplified.

In a transmission adapter as described here, the second coupling, in particular, is configured in order to be locked if the transmission adapter is mounted in an operating device.

The second coupling is configured in particular to be locked, in the sense that it cannot be opened or uncoupling is not possible if the transmission adapter is mounted in the operating device. Mechanical coupling between the transmission adapter and the proximal end of a transmission element is therefore possible only as long as the transmission adapter is mounted outside an operating device. Locking the second coupling makes possible, while respecting a predetermined sequence in dismantling or assembling components of a medical instrument, a reliable mechanical coupling of the transmission adapter with the proximal end of a transmission element. In particular, a medical instrument can be configured with the transmission adapter in such a way that in dismantling and assembling, the same hand gestures are required in the same sequence as those to be performed in a conventional instrument whose tool remains connected for some time with the distal end of the transmission element.

In a transmission adapter as described here, the proximal end of the transmission adapter, in particular, comprises a spherical-surface-shaped surface area. In particular, the proximal end of the transmission adapter essentially has the shape of a sphere. Thus the transmission adapter can make it possible to combine any kind of transmission element with a standard operating device, with a diameter of 2.5 mm for example, with a handling device from the applicant's product line offered under the designation "Clickline."

In particular, the transmission adapter is mounted inside the shaft and at its proximal end and is movable in relation to the shaft in translational and/or rotational manner. Integration of the transmission adapter into a shaft, in particular into a proximal area of the shaft, which is foreseen and configured for disposition in an operating device, can allow use or operation that is completely unchanged with respect to conventional medical instruments. Because as a rule each shaft is configured for a transmission element of a predetermined cross-section, the transmission adapter in the shaft can be adjusted without difficulty to the proximal end of the transmission element.

The transmission adapter can be integrated into the shaft in such a way that it cannot be removed from the shaft, or not without disturbance or not without the use of a tool, and therefore cannot be lost and is protected in the shaft from mechanical damage.

A shaft adapter includes a proximal end for coupling with a first part of an operating device, a distal end for coupling with a proximal end of a shaft, and a transmission adapter as described here that is movable with respect to the shaft adapter.

In particular, the transmission adapter is mounted inside the shaft adapter and is translationally and/or rotationally movable with respect to the shaft adapter. If the shaft adapter and in particular its distal end is configured for coupling with a proximal end of a predetermined shaft or a shaft of a predetermined type, the transmission adapter in the shaft adapter can be configured for coupling with a proximal end of a transmission element that is foreseen and configured for use with the predetermined shaft or with a shaft of the predetermined type. The shaft adapter can make possible a combination of a shaft (and thus of a transmission element) and operating device, which conventionally are not configured for combination with one another.

A shaft or shaft adapter with a transmission adapter with a movable gripper jaw, as described here, further includes, in particular, a lateral opening whereby the movable gripper jaw is mounted to be situated at least partly inside the contour of the shaft or of the shaft adapter if a proximal end of a transmission element is held positive-locked by the movable gripper jaw, and upon uncoupling of the transmission adapter from a proximal end of a transmission element, to extend beyond the contour of the shaft or shaft adapter.

The lateral opening, in particular, is mounted in an essentially cylindrical (in particular, circular-cylindrical) area of the shaft or shaft adapter. The shaft contour is, in particular, the contour or outer border of the cross-section of the shaft immediately proximal or immediately distal from the lateral opening. In particular, the shaft or shaft adapter in the area of the opening is essentially (that is, apart from the lateral opening) cylindrical or circular-cylindrical.

If the area of the shaft or shaft adapter that includes the lateral opening is mounted in a recess of corresponding shape in an operating device, the movable gripper jaw is held by the surface of the recess in the position holding the proximal end of a transmission element positive-locked and is prevented from being diverted out of this position. The mechanical coupling between the transmission adapter and the transmission element is thereby locked. Only if the shaft or shaft adapter is removed from the recess in the operating device, can the movable gripper jaws be diverted out of their position holding the proximal end of a transmission element positive-locked extending beyond the contour of the shaft or shaft adapter, thus producing or releasing the mechanical coupling between transmission adapter and transmission element.

A medical instrument includes an operating device having a first part and a second part, which is movable with respect to the first part; a shaft with a proximal end, which can be mechanically coupled with the first part of the operating device, and a distal end; a transmission element that can be moved within the shaft to transmit at least either a force or torque between the second part of the operating device and the distal end of the shaft; and a transmission adapter as is described here.

A tool can be provided on the distal end of the shaft or can be mechanically coupled with the distal end of the shaft. The transmission element is movable, in particular translationally and/or rotationally, within the shaft. The second part of the operating device can pivot, in particular, with respect to the first part.

In a medical instrument as is described here, the transmission adapter is, in particular, a component of a shaft as is described here or of a shaft adapter as described here.

A medical instrument as is described here includes, in particular, a number of alternatively usable transmission elements with variously configured proximal ends and a number of alternatively usable transmission adapters, such that the first couplings of all transmission adapters are configured identically and for releasable mechanical coupling with the second part of the operating device, such that the second couplings of the number of transmission adapters are of various configurations, and such that each transmission adapter comprises a second coupling, which is configured for releasable mechanical coupling with a proximal end of one of the transmission elements.

In particular, for every transmission element there exists a transmission adapter whose second coupling is configured for releasable mechanical coupling with the proximal end of the transmission element.

BRIEF DESCRIPTION OF THE DRAWINGS

Embodiments are described in greater detail hereinafter with reference to the appended drawings, which are as follows.

DETAILED DESCRIPTION OF THE INVENTION

Figure 1:
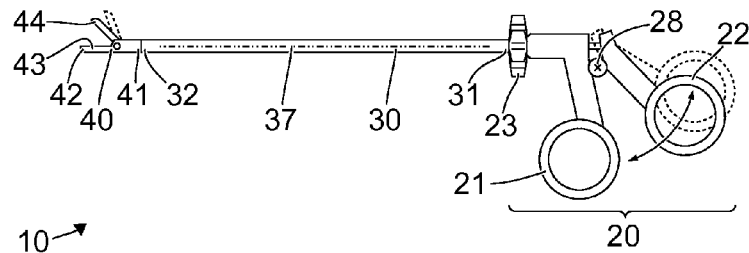
FIG. 1 shows a schematic depiction of a medical instrument.

FIG. 1 shows a schematic depiction of a medical instrument 10, in particular of a micro-invasive surgical instrument, having an operating device 20 at the proximal end, a shaft 30 and a tool 40.

The operating device includes a first or stationary part 21, a second or movable part 22, and a wheel 23. Said second part 22 is connected with said first part 21 by a joint in such a way that it is pivotable in relation to the first part 21 about a pivot axis 28 perpendicular to the plane of projection of FIG. 1.

The shaft 30 includes a proximal end 31, which is releasably mechanically coupled with the operating device 20, and a distal end 32, which is releasably mechanically coupled with the tool 40. The shaft 30 is rigid or flexible, straight or curved. In the illustrated example the shaft 30 is straight and has a longitudinal axis 37, with which the shaft 30 is rotation-symmetrical. The proximal end 31 of the shaft 30 is mechanically coupled with the wheel 23 in such a way that the shaft 30 and tool 40 can be rotated at the distal end 32 of the shaft 30 about the longitudinal axis 37 of the shaft 30 by means of the wheel 23.

The tool 40 comprises a proximal end 41, which is releasably mechanically coupled with the distal end 32 of the shaft 30, and a distal end 42. On the distal end 42 the tool 40 comprises a stationary jaw member 43 and a pivotable jaw member 44. Said pivotable jaw member 44 is coupled via a transmission rod, which is not illustrated in FIG. 1 and is movable within the shaft 30, with the second part 22 of the operating device 20 in such a way that a movement of the second part 22 of the operating device 20 with respect to the first part 21 causes a movement of the pivotable jaw member 44 with respect to the stationary jaw member 43 about a pivot axis perpendicular to the plane of projection of FIG. 1. For this purpose, the transmission rod, not shown in FIG. 1, is translationally movable, in particular within the shaft 30, parallel to the longitudinal axis 37 of the shaft 30, in order to transmit a tractive or pressure force between the second part 22 of the operating device 20 and the pivotable jaw member 44 of the tool 40. Alternatively or in addition, the transmission rod in the shaft 30 can be rotatable (in particular about the longitudinal axis 37 of the shaft 30) in order to transmit torque between the operating device 20 and the tool 40.

The pivotable jaw member 44 of the tool 40 in an open position and the second part 22 of the operating device 20 in a corresponding position are shown in solid lines in FIG. 1. In broken lines, the pivotable jaw member 44 of the tool 40 is shown in a fully open position and the second part 22 of the operating device 20 is shown in a corresponding position. If the second part 22 of the operating device 20 is pivoted, starting from the position shown in solid lines, in the direction toward the first part 21, the pivotable jaw member 44 of the tool 40 is pivoted, starting from the open position shown in solid lines, toward the stationary jaw member 43.

Figure 2:
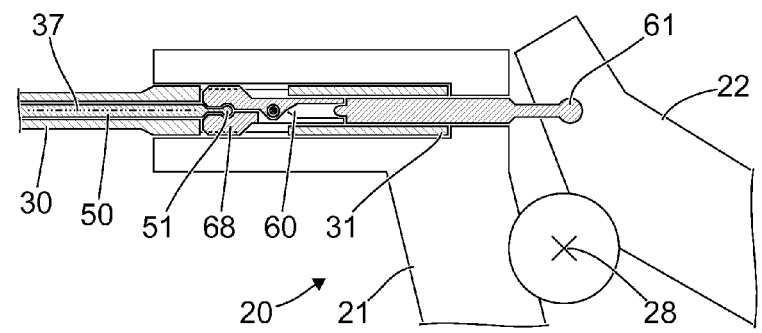
FIG. 2 shows a schematic depiction of a transmission adapter in a shaft.

FIG. 2 shows a schematic, enlarged depiction of a portion of the medical instrument 10 from FIG. 1. In particular, a section is shown through the proximal end 31 of the shaft 30 and through part of the operating device 20. The sectional plane contains the longitudinal axis 37 of the shaft 30. Sectional surfaces of the shaft 30, of a transmission or tractive rod or of a transmission element 50 and a transmission adapter 60 are shown with hatching. The parts 21, 22 of the operating device are sketched only in outline, to set them off more clearly from the shaft 30, transmission element 50 and transmission adapter 60. The wheel 23 indicated in FIG. 1 as well as devices for rotational coupling of the wheel 23 with the shaft 30 or with the transmission element 50 are not shown in FIG. 2.

The proximal end 31 of the shaft 30 is mounted in a recess of corresponding shape in the first part 21 of the operating device 20. The shaft 30 or its proximal end 31 can be releasably mechanically locked in the operating device 20 or its first part 21, for example by means of a spring-loaded handle, which is not shown in FIG. 2 and which engages in a recess on the shaft 30.

The shaft 30, similar to a tube, comprises a lumen in which the transmission element 50 is mounted. The lumen in the shaft 30 and the transmission element 50 each have an essentially circular-cylindrical shape. The cross-section of the lumen in the shaft 30 and the cross-section of the transmission element 50 are selected in such a way that the transmission element 50 is arranged so that it can slide in the shaft 30 in a direction parallel to the longitudinal axis 37 of the shaft 30 and can rotate about the longitudinal axis 37 with little play and friction. A proximal end 51 of the transmission element 50 has an essentially spherical configuration.

The transmission adapter 60 is disposed primarily inside the shaft 30 close to its proximal end 31. The transmission adapter 60 includes a first coupling 61 at its proximal end and a second coupling 68 at its distal end. The first coupling 61 has essentially the shape of a sphere and is coupled jointedly with the second part 22 of the operating device 20. When the second part 22 of the operating device 20 is in the position, illustrated in FIG. 2, which corresponds to the fully open position of the pivotable jaw member 44 of the tool 40 described above with reference to FIG. 1, the mechanical coupling between the first coupling 61 of the transmission adapter 60 and the second part 22 of the operating device 20 can be produced or released. Said mechanical coupling between the first coupling 61 of the transmission adapter 60 and the second part 22 of the operating device 20 corresponds, in particular, to a conventional mechanical coupling between the proximal end of a conventional transmission element and the pivotable part of a conventional operating device. Therefore no details of said mechanical coupling are described here.

The second coupling 68 at the distal end of the transmission adapter 60 is mechanically coupled with the proximal end 51 of the transmission element 50. Details are provided below with reference to FIGS. 5 through 8.

Figure 3:
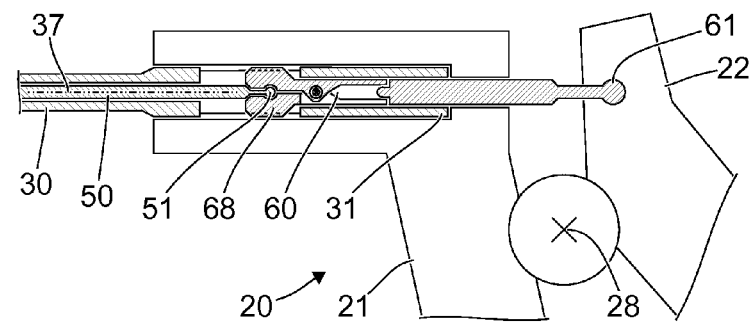
FIG. 3 shows an additional schematic depiction of the transmission adapter from FIG. 2.

The transmission element 50 and the transmission adapter 60 can slide parallel to the longitudinal axis 37 of the shaft 30. FIG. 3 shows another schematic depiction, which corresponds to FIG. 2 with respect to the illustrated features and the sectional plane. In contrast to the depiction in FIG. 2, however, the transmission element 50 and the transmission adapter 60 in FIG. 3 are pushed toward the proximal end. The second part 22 of the operating device 20 is accordingly pivoted about the pivot axis 28 (in clockwise direction).

A mechanical connection, which is releasable but in the unreleased condition is rigid (in particular, with little or no play), exists between the proximal end 51 of the transmission element 50 and the second coupling 68 of the transmission adapter 60. Therefore, every movement of the first coupling 61 and every force on the first coupling 61 of the transmission adapter 60 in the direction parallel to the longitudinal axis 37 of the shaft 30 is transmitted onto the transmission element 50 and from it to the distal end of the medical instrument 10 and to the tool 40, and vice versa.

Figure 4:
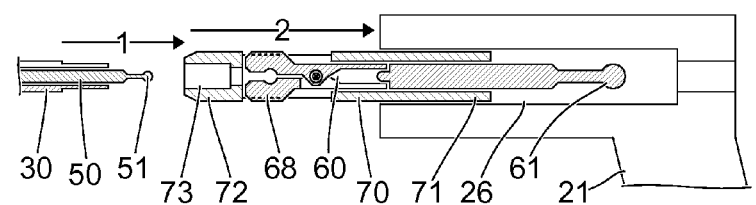
FIG. 4 shows a schematic depiction of a transmission adapter in a shaft adapter.

FIG. 4 shows a schematic depiction of a section through a shaft 30, a transmission element 50, a shaft adapter 70 and a transmission adapter 60 that is mounted in the shaft adapter 70. The type of depiction, in particular the illustrated sectional plane, corresponds essentially to that of FIGS. 2 and 3. To save space, only a portion of the first part 21 of the operating device is shown.

The embodiment in FIG. 4 is distinguished from the embodiments in FIGS. 2 and 3 in that the transmission adapter 60 is mounted, not in the proximal end 31 or in an area close to the proximal end 31 of the shaft 30, but rather in a separate shaft adapter 70. Said shaft adapter 70 comprises a proximal end 71 and a distal end 72 with a recess 73. Said shaft adapter 70 (similarly to a proximal area of the shaft 30, as in the embodiment in FIGS. 2 and 3) is configured for insertion in a recess 26 in the first part 21 of the operating device. Said recess 73 at the distal end 72 of the shaft adapter 70 is configured for insertion of the proximal end of the shaft 30.

Shown separately in FIG. 4 are the shaft 30 with the transmission element 50 on the one hand and the shaft adapter 70 with the transmission adapter 60 on the other hand, in addition to the first part 21 of the operating device. An arrow labeled as "1" indicates how the shaft 30 with the transmission element 50 can be inserted into the recess 73 at the distal end 72 of the shaft adapter 70 and the second coupling 68 of the transmission adapter 60. An arrow labeled "2" indicates how the shaft adapter 70 with the transmission adapter 60, which are shown in FIG. 4 only partly installed in the recess 26 in the first part 21 of the operating device, can be completely inserted into it. It is indicated below that, in particular, the coupling of the proximal end 51 of the transmission element 50 with the second coupling 68 of the transmission adapter 60 corresponding to the arrow "1" must occur before the complete insertion of the shaft adapter 70 with the transmission adapter 60 into the recess 26 in the first part 21 of the operating device.

FIGS. 5 through 8 show schematic, enlarged sectional depictions of a transmission adapter 60, which resembles in many features the transmission adapters described above with reference to FIGS. 2 through 4. The sectional planes of FIGS. 5 through 8 correspond to the sectional planes of FIGS. 2 through 4 and are parallel to the longitudinal axis 37 (compare FIGS. 1 through 3) of the shaft 30. The depiction in FIGS. 5 through 8 is distinguished by different positions and conditions of a transmission element 50 and of the transmission adapter 60.

The transmission adapter 60 is shown in FIGS. 5 through 8, in each case in a proximal area of a shaft 30 or in a shaft adapter 70. Because a shaft 30 and a shaft adapter 70 do not differ in the features illustrated in FIGS. 5 through 8 but rather only at the distal end (compare FIGS. 3 and 4), the following description with reference to FIGS. 5 through 8 applies both for a shaft and for a shaft adapter.

The transmission adapter 60 includes a base body 64 with a thrust bearing 67, a first gripper jaw 81 and a second gripper jaw 82. Said first gripper jaw 81 and second gripper jaw 82 form the second coupling 68 (compare FIGS. 2 through 4) of the transmission adapter 60. The first gripper jaw 81 and second gripper jaw 82 are connected jointedly with the base body 64 of the transmission adapter 60 and can pivot independently of one another about a pivot axis 88 perpendicular to the planes of projection of FIGS. 5 through 8. Details of the connection between the base body 64 and gripper jaws 81, 82 via the tie rods, which are not shown in FIGS. 5 through 8, are described below with reference to FIG. 13.

Figure 5:
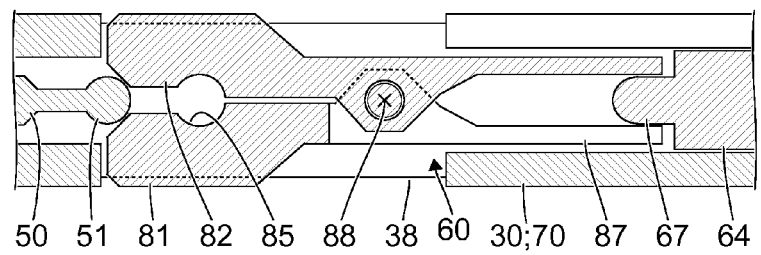
FIG. 5 shows a schematic depiction of a transmission adapter.

The shaft 30 or the shaft adapter 70 comprises two lateral openings 38 situated opposite one another. The gripper jaws 81, 82 are mounted partly in the openings 38 and in the positions shown in FIG. 5 are situated completely inside the contour of the shaft 30 or of the shaft adapter 70. Each gripper jaw 81, 82 is configured as a single piece with an associated elastic element 87. The elastic elements 87 are each bar-shaped. Ends of the elastic elements facing away from the gripper jaws 81, 82 are contiguous with the thrust bearing 67 on the base body 64 of the transmission adapter 60 or are supported on it. Forces or torque exerted by the elastic elements 87 on the gripper jaws 81, 82 hold them in the positions shown in FIG. 5 as long as no external force acts on them.

Figure 6:
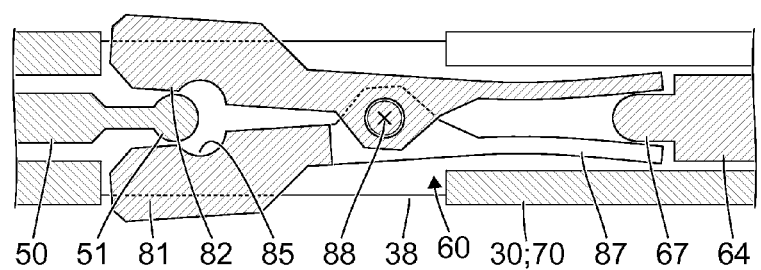
FIG. 6 shows an additional schematic depiction of the transmission adapter from FIG. 5.

If the proximal end 51 of the transmission element 50 is pushed in the proximal direction and thus is pressed against the gripper jaws 81, 82 (in particular, the indicated diagonal glide surfaces), the gripper jaws 81, 82 are diverted out of the positions shown in FIG. 5 into the positions shown in FIG. 6. In the process, the gripper jaws 81, 82 are pivoted in opposite directions about the pivot axis 88 and the elastic elements 87 are elastically reshaped. The elastic reshaping of the elastic elements 87 causes a return force or a return torque back to the positions of the gripper jaws 81, 82 shown in FIG. 5.

In the diversion of the gripper jaws 81, 82 shown in FIG. 6, the outer areas (in FIG. 6 the lower area of the first gripper jaw 81 and the upper area of the second gripper jaw 82) extend outward beyond the contour of the shaft 30 or of the shaft adapter 70.

If the transmission element 50, starting from the position shown in FIG. 6, is pushed farther in the proximal direction, the proximal end 51 of the transmission element 50 reaches recesses 85 in the gripper jaws 81, 82. The shape of the recesses 85 corresponds to the shape of the proximal end 51 of the transmission element 50. In particular, both the proximal end 51 of the transmission element 50 and the recesses 85 are spherical in shape. When the proximal end 51 of the transmission element 50 has reached its most proximal position in relation to the transmission adapter 60, the gripper jaws 81, 82 are moved by the elastic elements 87 into the positions shown in FIG. 7, which correspond completely or essentially to the positions shown in FIG. 5. The proximal end 51 of the transmission element 50 is situated in the recesses 85 in the gripper jaws 81, 82 and thus is held positive-locked by them.

As a result of a sufficient tractive force on the transmission element 50 in the distal direction, the proximal end 51 of the transmission element 50 can be released from the positive-locking connection with the gripper jaws 81, 82. As a result the gripper jaws 81, 82, against the forces or torque exerted by the elastic elements 87, are (temporarily) brought into the positions shown in FIG. 6.

Figure 7:
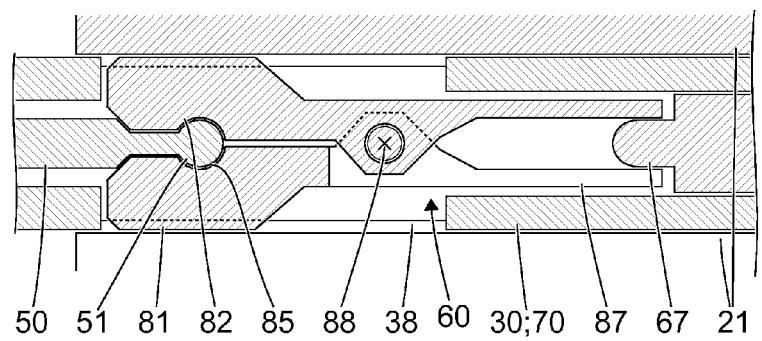
FIG. 7 shows an additional schematic depiction of the transmission adapter from FIGS. 5 and 6.
Figure 8:
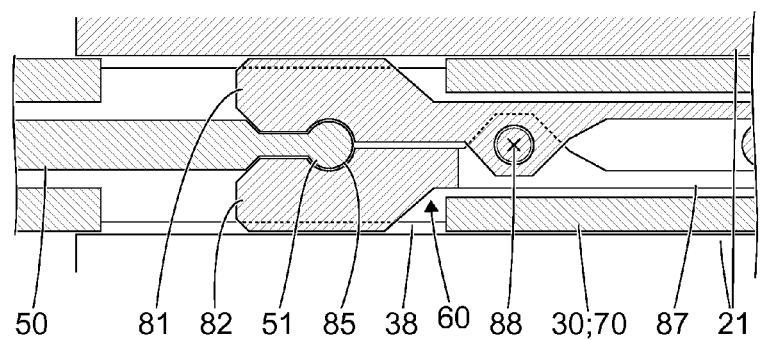
FIG. 8 shows an additional schematic depiction of the transmission adapter from FIGS. 5 through 7.

In FIGS. 7 and 8, the illustrated proximal area of the shaft 30 or shaft adapter 70 and the transmission adapter 60 are positioned in a recess in a part 21 of an operating device (compare FIGS. 2 through 4). In FIGS. 7 and 8, as a result, only the immediately bordering walls or areas of the part 21 of the operating device are indicated in each case. The gripper jaws 81, 82 are contiguous with the part 21 of the operating device and are prevented by it from being diverted into the positions shown in FIG. 6. The mechanical coupling between the proximal end 51 of the transmission element 50 and the coupling on the distal end of the transmission adapter 60 formed by the gripper jaws 81, 82 is thereby locked. The mechanical connection between the proximal end 51 of the transmission element 50 and the transmission adapter 60 can therefore be produced or severed only if the transmission adapter 60 together with the shaft 30 or shaft adapter 70 is situated outside the part 21 of the operating device.

The lateral openings 38 in the proximal area of the shaft 30 or in the shaft adapter 70 are substantially longer or have a length measured in the direction parallel to the longitudinal axis 37 of the shaft 30 (compare FIGS. 1 through 3) that is considerably greater than the areas of the gripper jaws 81, 82 mounted in the lateral openings 38. Therefore the gripper jaws 81, 82 can move in the direction parallel to the longitudinal axis of the shaft. In FIGS. 7 and 8, the transmission element 50 and the transmission adapter 60 are shown in different positions, which correspond in particular to different positions of the pivotable jaw member 44 (compare FIG. 1) of a tool at the distal end of the medical instrument.

Figure 9:
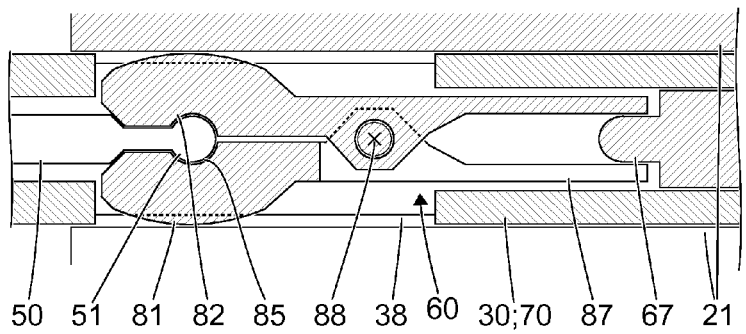
FIG. 9 shows a schematic depiction of an additional transmission adapter.

FIG. 9 shows a schematic depiction of an additional transmission adapter 60, which resembles in some features the transmission adapter described above with reference to FIGS. 5 through 8. The type of depiction, in particular the depicted sectional plane, corresponds to the depictions in FIGS. 5 through 8.

The transmission adapter 60 depicted in FIG. 9 is distinguished from the transmission adapter described above with reference to FIGS. 5 through 8, in particular, in that the external surfaces of the gripper jaws 81, 82 are convex, in particular cylindrical (with a cylindrical axis perpendicular to the plane of projection) or spherical.

Figure 10:
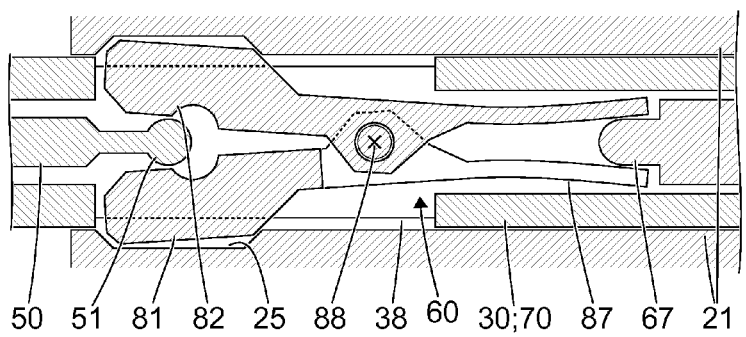
FIG. 10 shows a schematic depiction of an additional transmission adapter.

FIG. 10 shows a schematic depiction of an additional transmission adapter 60, which resembles in a few features the transmission adapters 60 described above with reference to FIGS. 5 through 9. The type of depiction, in particular the illustrated sectional plane, corresponds to the depictions in FIGS. 5 through 9.

Contrary to the properties and features described above with reference to FIGS. 7 and 8, the transmission adapter 60 from FIG. 10 is mounted in a part 21 of an operating device that comprises recesses 25. Said recesses 25 each have a shape that corresponds to the outlying areas of the gripper jaws 81, 82. Therefore, the gripper jaws 81, 82 in their most distal position, illustrated in FIG. 10, can be diverted into the positions, also illustrated in FIG. 6, in which a mechanical connection with the proximal end 51 of a transmission element 50 can be established or dissolved. If, on the other hand, the transmission adapter 60 with the gripper jaws 81, 82 is pushed in the proximal direction (compare FIG. 8), the mechanical coupling between the transmission element 50 and the transmission adapter 60 is locked, in similar manner as described above with reference to FIGS. 7 and 8.

Figure 11:
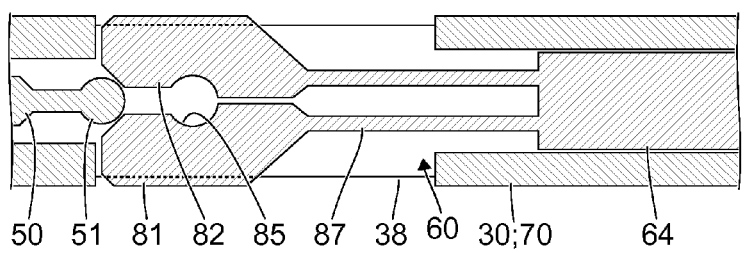
FIG. 11 shows a schematic depiction of an additional transmission adapter.

FIG. 11 shows a schematic depiction of an additional transmission adapter 60, which resembles in a few features the transmission adapters 60 presented above with reference to FIGS. 5 through 10. The depiction in FIG. 11 corresponds, particularly with respect to the illustrated sectional plane, to the depictions in FIGS. 5 through 10.

In the embodiment in FIG. 11, the elastic elements 87 are configured as solid-state joints, which connect the base body 64 with the gripping jaws 81, 82 as a single piece. The elastic elements 87 thus simultaneously fulfill two functions, namely the jointed connection with the base body 64 and the return effect.

Figure 12:
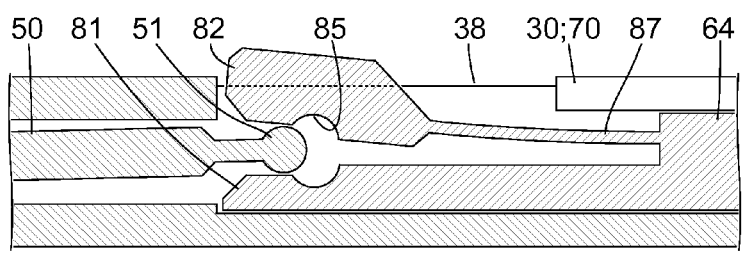
FIG. 12 shows a schematic depiction of an additional transmission adapter.

FIG. 12 shows a schematic depiction of an additional transmission adapter 60, which resembles in a few features the transmission adapters 60 presented above with reference to FIGS. 5 through 11. The depiction in FIG. 12 corresponds, particularly with respect to the illustrated sectional plane, to the depictions in FIGS. 5 through 11.

The embodiment in FIG. 12 is distinguished from the embodiments described above with reference to FIGS. 5 through 11 in particular in that the first gripper jaw 81 is rigidly connected with the base body 64 of the transmission adapter 60. Only the second gripper jaw 82 is jointedly connected with the base body 64, and in the illustrated example this occurs by an elastic element 87 configured as a solid-state joint. In forming or releasing a mechanical connection between the transmission element 50 and the transmission adapter 60, only a diversion of the second gripper jaw 82 occurs. In accordance with this asymmetrical process, a diversion of the transmission element 50, in particular of its proximal end 51, is required, as can be recognized in FIG. 12.

Figure 13:
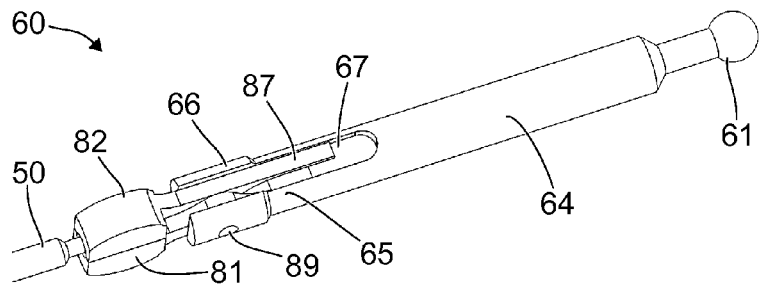
FIG. 13 shows a schematic depiction of an additional transmission adapter.
Figure 14:
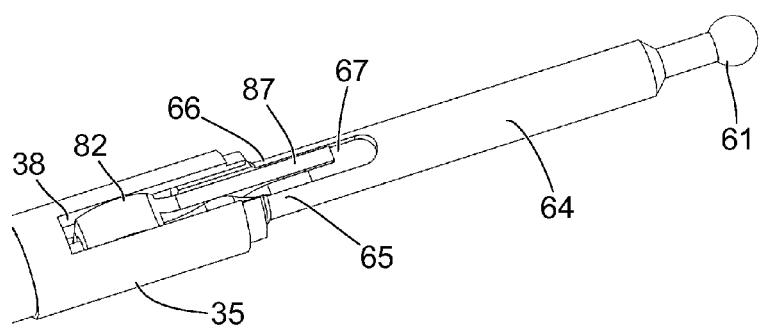
FIG. 14 shows an additional schematic depiction of the transmission adapter from FIG. 13.
Figure 15:
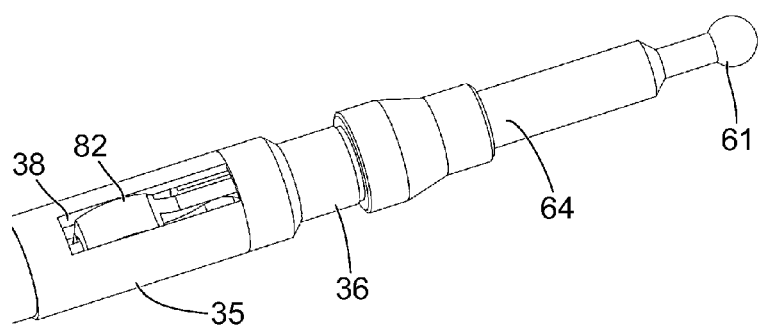
FIG. 15 shows an additional schematic depiction of the transmission adapter from FIGS. 13 and 14.

FIGS. 13 through 15 show schematic axonometric depictions of a transmission adapter 60, which corresponds in a few features to the transmission adapters presented above with reference to FIGS. 5 through 10, in particular to the transmission adapter described above with reference to FIG. 9.

FIG. 13 shows only the transmission adapter 60 with a mechanically coupled transmission element 50. The base body 64 of the transmission adapter 60 comprises the spherical-shaped first coupling 61 at its proximal end and two tie rods 65, 66 in fork-like arrangement at its distal end. The gripper jaws 81, 82 are connected with the tie rods 65, 66 by an axle 89 parallel to their pivot axis 88 (compare FIGS. 5 through 10). Each end of the axle 89 is joined with a tie rod 65, 66. Mounting the gripper jaws 81, 82 on the axle 89 makes the described pivotability possible. The elastic elements 87 that are configured in a single piece with the gripper jaws 81, 82 are contiguous with the thrust bearing 67 on the base body 64.

In FIG. 14 the distal end of the transmission adapter and, in particular, the gripper jaws 82 are mounted in a distal sleeve 35. In FIG. 15 the distal sleeve 35 is supplemented by a proximal sleeve 36 to the proximal area of a shaft (or of a shaft adapter). The lateral openings 38, in which the gripper jaws 82 are partly mounted, are formed by longitudinal slits in the distal sleeve 35.

Otherwise than as indicated in FIGS. 2 through 12, the proximal area of the shaft formed by the sleeves 35, 36, in particular by the proximal sleeve 36, does not comprise a circular-cylindrical cross-section. A broad, flat ring-shaped groove makes possible a positive locking of a mechanical connection of the shaft with an operating device by devices that are not shown in FIGS. 1 through 12.

In the embodiments described above with reference to FIGS. 2 through 15, the second coupling 68 includes two gripper jaws 81, 82 in each case, of which at least one is pivotable. Alternatively, the second coupling 68 can include one or more gripper jaws, which can move or slide along a predetermined straight or curved pathway. A gripping jaw can be simultaneously pivotable and movable along a predetermined path. A pathway is predetermined, for example, by a link or a similar guide, which can couple a translational movement with a pivoting movement.

Figure 16:
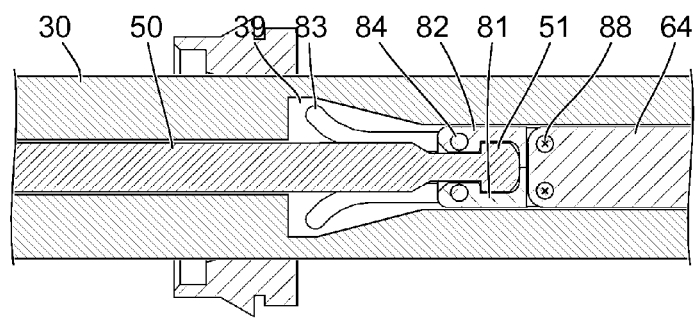
FIG. 16 shows a schematic depiction of an additional transmission adapter.

FIG. 16 shows a schematic depiction of a section through an additional transmission adapter. The sectional plane is parallel to the plane of projection of FIG. 1 and corresponds essentially to the sectional planes of FIGS. 2 through 12. Similarly as in FIGS. 5 through 12, only the distal end of the transmission adapter is illustrated. The proximal end of the transmission adapter corresponds, for example, to the proximal end described above with reference to FIGS. 2 through 4.

The second coupling of the transmission adapter, illustrated in FIG. 16, includes two gripper jaws 81, 82. Each gripper jaw can pivot about a pivot axis 88 perpendicular to the sectional plane of FIG. 16. Each pivot axis 88 is defined by a pin, bolt or axle, by means of which the gripper jaw 81, 82 is jointedly connected with a base body 64 of the transmission adapter.

The transmission adapter is mounted in a shaft 30, in particular in a proximal area of the shaft 30. The lumen of the shaft 30, in which a transmission element 50 is positioned, is widened to form a cavity that also receives the transmission adapter. The distal end 39 of the cavity is configured in order to make it possible for the gripper jaws 81, 82 to pivot outward when the transmission adapter with the base body 64 and the gripper jaws 81, 82 is pushed in the distal direction with respect to the position shown in FIG. 16.

Link guides 83 are mounted close to the distal end 39 of the cavity. Said link guides 83 each comprise an essentially straight proximal portion and a curved distal portion. Mounted on each gripper jaw 81, 82 close to its distal end is a pin 84, which engages in one of the link guides 83. By means of the link guides 83 and the pins 84 that engage in said link guides 83, a linear movement of the transmission adapter between a proximal position shown in FIG. 16 and a distal position is coupled with a pivot movement of the gripper jaws 81, 82 around their pivot axes 88. With the transmission adapter in the proximal position shown in FIG. 16, the gripper jaws 81, 82 in an area distally from this position are situated in the gripping or holding positions shown in FIG. 16, in which they hold the proximal end 51 of the transmission element 50 in positive-locking connection. In an extremely proximal area, the gripper jaws 81, 82 pivot away from one another and release the proximal end 51 of the transmission element 50.

Figure 17:
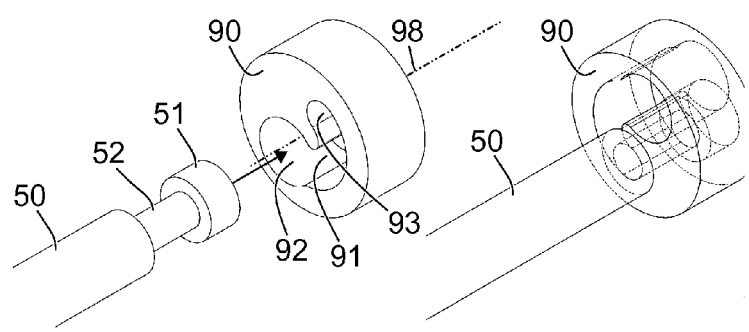
FIG. 17 shows a schematic depiction of an additional transmission adapter.

FIG. 17 shows two schematic axonometric depictions of an additional transmission adapter. In particular, a coupling member 90 of the transmission adapter is shown, which can be coupled with a proximal end 51 of a transmission element. Additional elements and components of the transmission adapter and a shaft or shaft adapter, in which the transmission adapter can be mounted, are not illustrated.

The coupling member 90 can rotate about a rotation axis 98, which is essentially parallel to the longitudinal axis of a transmission element 50 that is to be coupled with the coupling member 90. Said coupling member 90 comprises an opening or recess 91 with a first end 92 and a second end 93. The first end 92 has a cross-section (based on a plane perpendicular to the rotation axis 98), which is adjusted to the proximal end 51 of the transmission element 50. The proximal end 51 of the transmission element 50 cannot therefore be fed through the first end 92 of the recess 91 if the first end 92 of the recess 91 is oriented to the proximal end 51 of the transmission element 50 in the manner shown in FIG. 17, at left.

The second end 92 of the recess 91 has a cross-section that is adjusted to the cross-section of a neck 52 distal from the proximal end 51 of the transmission element 50. Therefore the rotatable coupling member 90 can be rotated about its rotation axis 98 into the position shown at the right in FIG. 17 if the neck 52 of the transmission element is situated in the recess 91. With the rotatable coupling member 90 in the position shown to the right in FIG. 17, the transmission element 50 is coupled in positive-locking connection with the coupling member 90.

Figure 18:
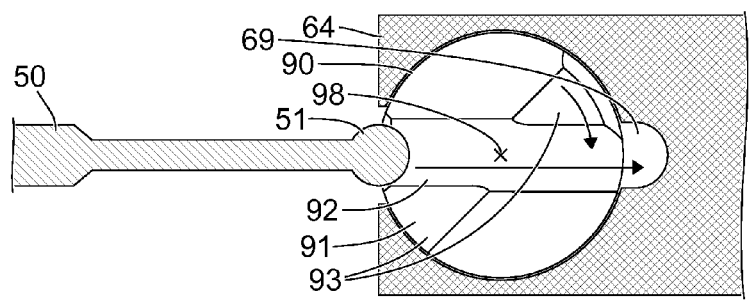
FIG. 18 shows a schematic depiction of an additional transmission adapter.
Figure 19:
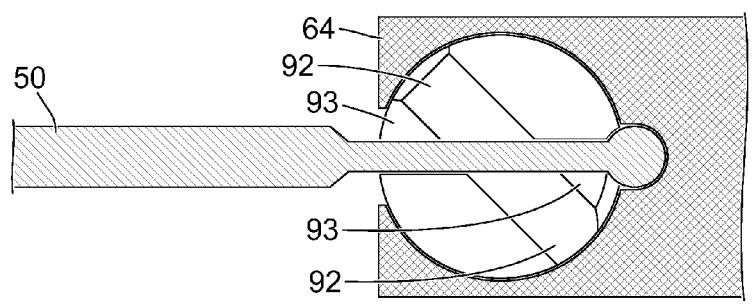
FIG. 19 shows an additional schematic depiction of the transmission adapter from FIG. 18.

FIGS. 18 and 19 show schematic sectional depictions of an additional transmission adapter. In particular, a distal end of the transmission adapter is shown with a coupling to couple with a proximal end 51 of a transmission element 50. A proximal end of the transmission adapter, not shown in FIGS. 18 and 19, corresponds for example to the proximal end described above with reference to FIGS. 2 through 4. The sectional plane is parallel to the plane of projection of FIG. 1 and corresponds essentially to the sectional planes of FIGS. 2 through 12 and FIG. 16.

The transmission adapter includes, in a base body 64, a coupling member 90, which can be rotated about a rotation axis 98 perpendicular to the sectional plane of FIGS. 18 and 19. The coupling member 90 is shown in FIGS. 18 and 19 in two different positions. The coupling member 90 has an essentially circular cross-section and is mounted in a corresponding cavity in the base body 64. The coupling member 90 comprises a recess 91, which penetrates all the way through the coupling member 90 parallel to the sectional plane of FIGS. 18 and 19 from the distal to the proximal end.

The recess includes an essentially circular-cylindrical through-borehole 92, which comprises at each end a keyhole-type widening 93 in the counterclockwise direction and parallel to the sectional plane of FIGS. 18 and 19. With respect to its mechanical reciprocal action with the transmission element 50 or its proximal end 51, the circular-cylindrical through-borehole 92 corresponds to the first end and the keyhole-type widenings 93 correspond to the second end of the recess in the rotatable coupling member of the embodiment from FIG. 17.

With the coupling member 90 in the position shown in FIG. 18, the through-borehole 92 is parallel to the longitudinal axis of the transmission element 50. The proximal end 51 of the transmission element 50, as indicated by a straight arrow, can be guided through the through-borehole 92 into a niche 69 in the base body 64. Thereafter, the coupling member 90, as indicated by a curved arrow, can be rotated about its rotation axis 98 into the position shown in FIG. 19. With the coupling member 90 in the position shown in FIG. 19, the proximal end 51 of the transmission element is held positive-locked in the niche 69 by the coupling member 90.

What is claimed is:

1. A transmission adapter for a medical instrument, the medical instrument having a shaft, a transmission element, which can move within the shaft, and an operating device with a first part, which can be mechanically rigidly coupled with a proximal end of the shaft, and a second part, which can move with respect to the first part, wherein the transmission adapter comprises:

"first coupling for releasable mechanical coupling with the second part of tile operating device; and
a second coupling for releasable mechanical coupling with a proximal end of the transmission element;
wherein the transmission adapter is fully separable from the operating device and from the transmission element.

2. The transmission adapter according to claim 1, wherein the second coupling includes a movable gripper jaw for positive-locking or friction-locked holding of the proximal end of the transmission element.

3. The transmission adapter according to claim 2, wherein the movable gripper jaw pivots about a pivot axis.

4. The transmission adapter according to claim 2, wherein the movable gripper jaw is movable along a predetermined path.

5. The transmission adapter according to claim 2, further comprising:
an elastic element configured to mechanically pre-tense the movable gripper jaw to a position that grips the proximal end of the transmission element.

6. The transmission adapter according to claim 1, wherein the second coupling comprises a rotatable coupling member, such that said rotatable coupling member is rotatable between a first position, in which a mechanical coupling with the proximal end of the transmission element can be produced and released, and a second position, in which a mechanical coupling with the proximal end of the transmission element is locked.

7. The transmission adapter according to claim 1, wherein the transmission adapter is integrated into a proximal area of the shaft.

8. The transmission adapter according to claim 1, wherein the second coupling is locked when the transmission adapter is mounted in the operating device.

9. The transmission adapter according to claim 1, wherein the first coupling of the transmission adapter comprises a spherical-surface-shaped surface portion.

10. A shaft for a medical instrument, comprising:
a proximal end for coupling with a first part of an operating device;
a distal end for coupling with a tool; and,
a transmission adapter, which is movable with respect to the shaft and which includes a first coupling for releasable mechanical coupling with a second part of the operating device, and a second coupling for releasable mechanical coupling with a proximal end of a transmission element, wherein the transmission element can move within the shaft,
wherein the transmission adapter is fully separable from the operating device and from the transmission element.

11. A shaft adapter, comprising:
a proximal end for coupling with a first part of an operating device a distal end for coupling with a proximal end of a shaft; and
a transmission adapter, which is movable with respect to the shaft adapter and which includes a first coupling for releasable mechanical coupling with a second part of the operating device, and a second coupling for releasable mechanical coupling with a proximal end of a transmission element, wherein the transmission element can move within the shaft,
wherein the transmission adapter is fully separable from the operating device and from the transmission element.

12. A shaft for a medical instrument, comprising:
a proximal end for coupling with a first part of an operating device;
a distal end for coupling with a tool; and,
a transmission adapter which is movable with respect to the shaft and includes:
a first coupling for releasable mechanical coupling with a second part of the operating device; and,
a second coupling for releasable mechanical coupling with a proximal end a transmission element;
wherein the second coupling includes a movable gripper jaw for positive-locking or friction-locked holding of the proximal end of the transmission element; and,
wherein the shaft further comprises:
a lateral opening, such that the movable gripper jaw is mounted at least partly in the lateral opening, such that the movable gripper jaw is configured to be situated entirely within a contour of the shaft or shaft adapter when the proximal end of the transmission element is held positive-locked by the movable gripper jaw, and to extend above the contour of the shaft or shaft adapter upon the uncoupling of the transmission adapter from a the proximal end of a the transmission element;
wherein the transmission adapter is fully separable from the operating device and from the transmission element.

13. A medical instrument, comprising:
an operating device with a first part and a second part, the second part being movable with respect to the first part;
a shaft with a proximal end and a distal end, the proximal end of the shaft being mechanically coupled with the first part of the operating device,
a transmission element for transmitting at least either a force or torque between the second part of the operating device and the distal end of the shaft the transmission element being movable within the shaft; and,
a transmission adapter which includes a first coupling for releasable mechanical coupling with the second part of the operating device, and a second coupling for releasable mechanical coupling with a proximal end of the transmission element, wherein the transmission adapter is fully separable from the operating device and from the transmission element.

14. The medical instrument according to claim 13, wherein the transmission adapter is a component of at least one of the group consisting of the shaft and a shaft adapter having a proximal end for coupling with the first part of the operating device and a distal end for coupling with the proximal end of the shaft.

15. A medical instrument according to claim 13, comprising:
a number of alternatively usable transmission elements with proximal ends of various configuration; and,
a number of alternatively usable transmission adapters,
such that the first couplings of all transmission adapters are configured equally and for releasable mechanical coupling with the second part of the operating device,
such that the second couplings of the number of alternatively usable transmission adapters are of various configuration, and
such that each of the second couplings of the alternatively usable transmission adapters is configured for releasable mechanical coupling with a proximal end of one of the alternatively usable transmission elements.

* * * * *

UNITED STATES PATENT AND TRADEMARK OFFICE
CERTIFICATE OF CORRECTION

PATENT NO. : 8,876,805 B2
APPLICATION NO. : 13/734740
DATED : November 4, 2014
INVENTOR(S) : Daniel Kärcher Page 1 of 1

It is certified that error appears in the above-identified patent and that said Letters Patent is hereby corrected as shown below:

In the Claims

Column 15, Lines 1-2 reads:
""first coupling for realeasable mechanical coupling with the"

Should read:
-- a first coupling for releasable mechanical coupling with the --

Signed and Sealed this
Twenty-eighth Day of March, 2017

Michelle K. Lee
*Director of the United States Patent and Trademark Office*